(12) United States Patent
Cotton

(10) Patent No.: US 8,852,134 B2
(45) Date of Patent: Oct. 7, 2014

(54) PORTABLE SPLINT SYSTEM

(76) Inventor: Gerald Cotton, Winfield, IL (US)

( * ) Notice: Subject to any disclaimer, the term of this patent is extended or adjusted under 35 U.S.C. 154(b) by 1014 days.

(21) Appl. No.: 11/161,060

(22) Filed: Jul. 21, 2005

(65) Prior Publication Data
US 2007/0021702 A1 Jan. 25, 2007

(51) Int. Cl.
*A61F 5/00* (2006.01)

(52) U.S. Cl.
USPC .................................. 602/32; 602/5

(58) Field of Classification Search
USPC ............ 602/4, 5, 16, 23, 26–29, 32; 128/882; 5/651
See application file for complete search history.

(56) References Cited

U.S. PATENT DOCUMENTS

| | | | |
|---|---|---|---|
| 432,888 A | 7/1890 | Miller | |
| 1,890,372 A | 12/1932 | Ettinger | |
| 1,904,942 A * | 4/1933 | Heigl | 602/35 |
| 1,978,752 A | 10/1934 | Lange | |
| 2,007,127 A | 7/1935 | Longfellow | |
| 2,052,990 A | 9/1936 | Siebrandt | |
| 2,926,662 A * | 3/1960 | Pile | 602/16 |
| 3,066,322 A | 12/1962 | Derby | |
| 3,417,748 A | 12/1968 | Bimler | |
| 3,616,795 A | 11/1971 | Powlan | |
| 3,651,803 A * | 3/1972 | Bimler | 602/16 |
| 3,661,150 A | 5/1972 | Peterssen et al. | |
| 3,762,405 A * | 10/1973 | De George | 602/23 |
| 3,765,411 A | 10/1973 | Ward, Jr. | |
| 3,800,787 A | 4/1974 | Rush | |
| 3,848,589 A | 11/1974 | Throner | |
| 3,878,842 A | 4/1975 | Goldberg | |
| 4,323,060 A | 4/1982 | Pecheux | |
| 4,328,794 A | 5/1982 | Holmes | |
| 4,336,796 A | 6/1982 | Andrews et al. | |
| 4,419,991 A | 12/1983 | Lee | |

(Continued)

FOREIGN PATENT DOCUMENTS

| | | |
|---|---|---|
| AU | 700537 | 4/1997 |
| GB | 371571 | 4/1932 |

(Continued)

OTHER PUBLICATIONS

Arizona Universal Leg Splint; Instructions for use include illustrations 1-4. Designed by Robert G. Volz, Tucson, Arizona (2 pages).

(Continued)

*Primary Examiner* — Michael A. Brown
(74) *Attorney, Agent, or Firm* — Law Office of Marc D. Machtinger, Ltd.

(57) ABSTRACT

A portable splint system is disclosed. The portable splint system has a limb supporting splint having at least two sections, each section has a substantially continuous cover plate, each cover plate having a concave contoured upper surface for cradling a splinted limb. A locking hinge connects the sections of the limb supporting splint. The limb supporting splint may also have one or more vertical support arches mounted thereon. The limb supporting splint is suitable for use in a bed or overhead traction apparatus. The portable splint system also includes a portable base unit onto which the limb supporting splint may be attached. The portable base unit has a stabilizing frame, height adjusters for independently adjusting the height of the proximal end of the limb supporting splint and the distal end of the limb supporting splint, and traction weight supports.

4 Claims, 6 Drawing Sheets

(56) References Cited

U.S. PATENT DOCUMENTS

| | | | |
|---|---|---|---|
| 4,620,698 A * | 11/1986 | Reed et al. .................. 5/651 |
| 4,627,423 A | 12/1986 | Kampner |
| 4,649,907 A | 3/1987 | Whitehead et al. |
| 4,664,099 A | 5/1987 | Pearl, Jr. |
| 4,782,827 A * | 11/1988 | Paratte .................. 602/35 |
| 5,002,046 A | 3/1991 | Scott |
| 5,316,544 A | 5/1994 | McAninch |
| 6,533,744 B1 | 3/2003 | Stanish et al. |

FOREIGN PATENT DOCUMENTS

| | | |
|---|---|---|
| GB | 417997 | 10/1934 |
| GB | 1123105 | 8/1968 |
| GB | 1188467 | 4/1970 |
| GB | 1471648 | 4/1973 |

OTHER PUBLICATIONS

Böhler-Braun Splint Frame; Illustration including list of components (1 page).

Thomas Leg Splint Basic Frame Setup; Illustration including list of components (1 page).

* cited by examiner

PORTABLE SPLINT SYSTEM

FIELD OF THE INVENTION

The present invention relates to traction splints. Specifically, the present invention relates to portable traction splints.

DESCRIPTION OF THE RELATED ART

The use of traction to facilitate the healing of fractured limbs has been practiced for some time. Typically the limb is secured, through the use of bandages, wraps and the like, to a splint. Traction force is applied to the limb through the use of wires, ropes or cables attached to the limb or splint at one end and a weight at the other end. The modern practice of applying traction to fractured limbs dates back to the mid-1800's and Dr. Hugh Owen Thomas. Dr. Thomas advocated the prolonged uninterrupted rest for the treatment of fractures. His "Thomas Splint" was introduced to the battlefields of World War I, where it is credited with the reducing the fatality rate from compound fractures from about eighty percent to about twenty percent.

The Thomas splint consists of a proximal ring that fits around the upper leg and to which two long rigid slender steel rods are attached. The rods extend down to another smaller ring distal to the foot. Traction using the Thomas splint uses fixed traction with the counter traction being applied through the proximal ring of the splint. A Thomas splint and fixed traction is capable of maintaining a reduction previously achieved by manipulation. It is the splint which controls the alignment, not the traction. Traction is used to balance the resting muscle tone. Typically the splint is suspended using an overhead beam in such a way as to enable the splint to move with the patient when the patient moves in bed.

Generally speaking, traction splint systems can be divided into two categories: overhead or bed mounted splint systems, and portable splint systems. Overhead or bed mounted splint systems are characterized by a bed or ceiling mounted support frame which supports a network of ropes, pulleys, and weights all of which act to impart traction force on a splinted limb. An example of a bed mounted splint system can be seen in U.S. Pat. No. 5,316,544, FIG. 1. As shown, the patient is in prone in the bed, his splinted leg supported in a Thomas splint. An overhead frame is attached to the head and foot of the bed. Suspended from the overhead frame are various ropes, pulleys and weights, which support the splinted led up off the bed surface and impart a traction force on the splinted leg.

Overhead traction splint systems typically allow for more control in the application of the traction forces applied to the patient. Overhead systems generally allow for a greater number of rope, pulley, and weight combinations, thus allowing the customization of the traction force magnitude and direction to the patient's specific needs. Additionally, overhead splint systems are capable of treating multiple fracture sites simultaneously, such as a pelvic fracture and a tibia-fibula fracture. The position and orientation of the splint within the system is also adjustable, further increasing the flexibility of the overhead systems. However, because of their fixed nature, overhead splint systems do not lend themselves to continently moving the patient from one location to another.

Portable splint systems are characterized by a frame or stand that rests on a patient's bed. Attached to the frame or stand are weights, ropes, and pulleys that act to impart traction force on a splinted limb. An example of a portable splint system is disclosed in U.S. Pat. No. 3,661,150, issued to Peterssen et al. (Peterssen). Peterssen discloses a splint for the treatment of fractured legs. The splint includes a frame, which rests on a bed or other surface, a support for the femur pivotally connected to the frame and a support for the tibia-fibula pivotally connected to the femur support. The supports are designed as frames covered with cloth. Two upright portions support a holding member which is provided with pulleys over which cables extend for carrying the support for the femur and the support for the tibia-fibula.

Portable splint systems allow the patient to be treated in locations where overhead systems are not present and, as the name implies, they are portable, that is, they can be moved from one location to another. The attractiveness of portable splint systems is that they can be moved with the patient when the patient is taken for lab work or test outside of the hospital room. However, because of their relatively compact size, portable splint systems do not allow the flexibility and customization that overhead systems provide. For example, many portable splint systems are not suitable for treating a patient with a fused knee. Additionally, portable splint systems are generally not capable of treating multiple fractures simultaneously.

The lack of portability of overhead splint systems and the limited flexibility of portable splint systems often leads to doctors prescribing treatment using an overhead system when the patient is in the hospital bed and a portable splint system when the patient is being transported or treated out of the hospital bed. This use of dual systems can lead to complications in the treatment of splinted limbs. Complications from transporting a patient from an overhead system to a portable system can include, but is not limited to, collapse of the fracture site, bleeding, and deep vein thrombosis.

In several splint systems, whether portable or overhead, the ring under the patient's thigh is attached by a swivel so that the frame can be used for either leg. This causes complications of its own. Particularly, since the ring is moveable, when the patient slides down in the bed, the ring can dig into the mattress. This digging into the mattress causes the ring to flatten out. As a result, the patient ends up sitting on the edge of the ring. Prolonged contact between the ring and patient in this manner can cause the patient's skin to break down, particularly under the gluteal fold.

Furthermore, patient hygiene can become problematic with current splint systems. For example, changing bed linens for a bed stricken patient in a portable splint system often requires the caregiver to move the patient in such a manner that either interrupts the applied traction, causes the knee or other joints to move in such a manner as to affect the alignment of the fracture or both. Accordingly, the frequency of bed linen changes is often reduced and as a result patient hygiene suffers.

As Dr. Thomas recognized nearly 150 years ago, fractures heal best when treatment is uninterrupted. With this in mind, there remains a need for an improved splint system that can be used in an overhead splint arrangement and as a portable splint. Furthermore, there remains a need for portable splint system having increased flexibility and allowing treatments typically only available in an overhead system. Thus, it would be advantageous to provide an improved splint system that can be used in an overhead splint arrangement and as a portable splint. It would also be advantageous to provide a portable splint system having increases flexibility and allowing treatments typically available in an overhead system.

SUMMARY

In view of the deficiencies described above, it is an object of the present invention to provide an improved splint system that can be used in an overhead splint arrangement and as a portable splint system.

It is a further object of the present invention to provide a portable splint system that can be used to maintain continuous traction on a fracture site.

It is a further object of the present invention to provide a portable splint system that allows for the treatment of patients with fused knees.

It is a further object of the present invention to provide a portable splint system that allows for easy access to the patient to improve patient hygiene.

It is a further object of the present invention to provide a portable splint system that allows for the treatment of multiple fractures simultaneously.

It is a further object of the present invention to provide a portable splint system that decreases the chances of the fracture site collapse, bleeding, and deep vein thrombosis.

The portable splint system of the present invention has a limb supporting splint having at least two sections, each section has a substantially continuous cover plate, each cover plate having a concave contoured upper surface for cradling a splinted limb. A locking hinge connects the sections of the limb supporting splint. The limb supporting splint may also have one or more vertical support arches mounted thereon. The limb supporting splint is suitable for use in a bed or overhead traction apparatus known in the art.

The portable splint system also includes a portable base unit onto which the limb supporting splint may be attached. Thus, limb supporting splint may be used in both an overhead traction apparatus and as part of the portable splint system of the present invention. The portable base unit has a stabilizing frame, height adjusters for independently adjusting the height of the proximal end of the limb supporting splint and the distal end of the limb supporting splint, and traction weight supports.

In various preferred embodiments the stabilizing frame 190 is a substantially rectangular and has cross bracing and provisions for mounting the height adjusters. Ideally, the stabilizing frame is sized to fit onto a hospital or bed or similarly sized object, such as a gurney, x-ray table and the like. Furthermore, the stabilizing frame should be sufficiently sized to resist movement and tipping of the portable splint system while in use.

The limb supporting splint can be attached to the portable base unit in a variety of ways. In various preferred embodiments, a distal facing hook associated with the height adjuster associated with the distal end of the limb supporting splint and a proximal facing hook associated with the height adjuster associated with the proximal end of the limb support splint are used to connect the portable base unit to the limb supporting splint. In this arrangement, a distal clamping system is used to secure a distal connecting rod on the limb supporting splint into the distal facing hook and a proximal clamping system is used to secure a proximal connecting rod on the limb supporting splint.

In addition to the system described above, the present invention also includes a method of transferring a splinted patient from a bed mounted traction apparatus to a portable splint system. First, a limb supporting splint in a bed mounted traction apparatus is secured to a portable base unit. Next, traction force from the bed mounted traction apparatus is transferred to the portable base unit without removal of the traction force. By using this method, continuous traction is maintained, which reduces the chances of a fracture collapse, bleeding and deep vein thrombosis.

Other features and advantages of the invention will be apparent from the following detailed description taken in conjunction with the following figures, wherein like reference numerals represent like features.

DETAILED DESCRIPTION OF THE INVENTION

Figure 1:
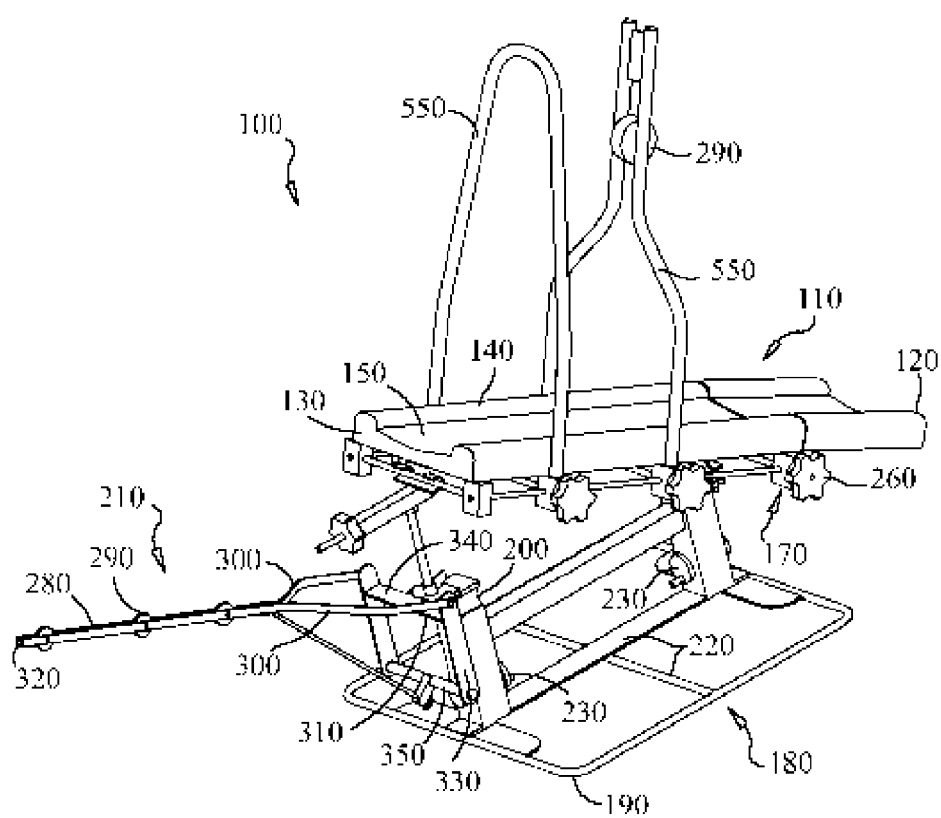
FIG. 1 shows a portable splint system according to the present invention.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

Figure 2:
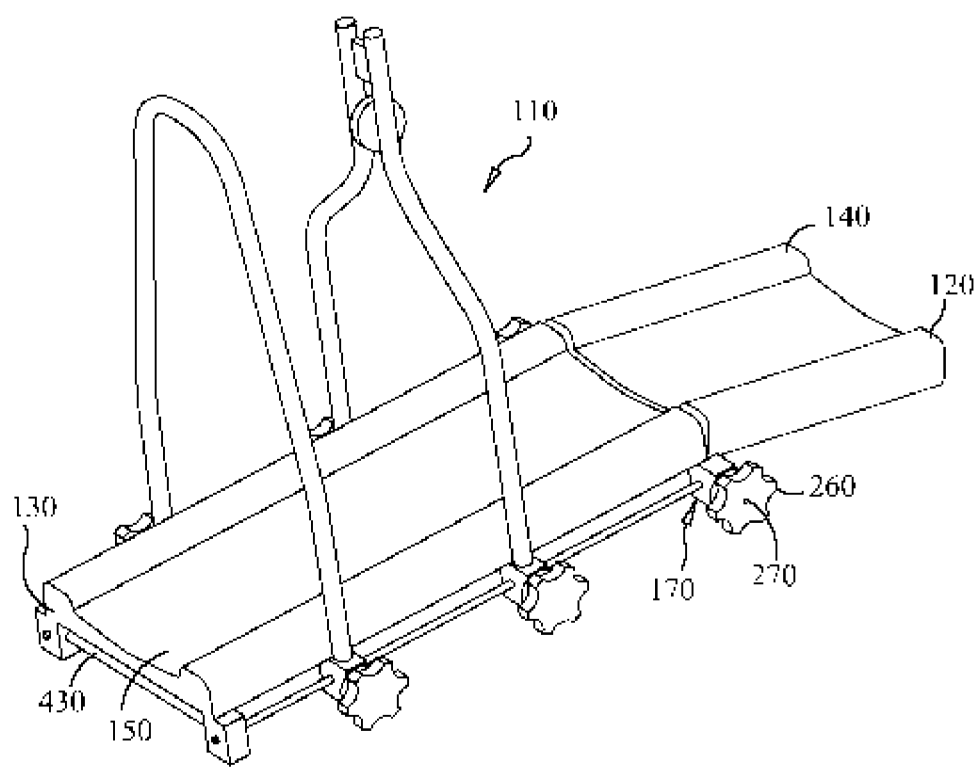
FIG. 2 shows a limb supporting splint of a portable splint system according to the present invention.
Figure 3:
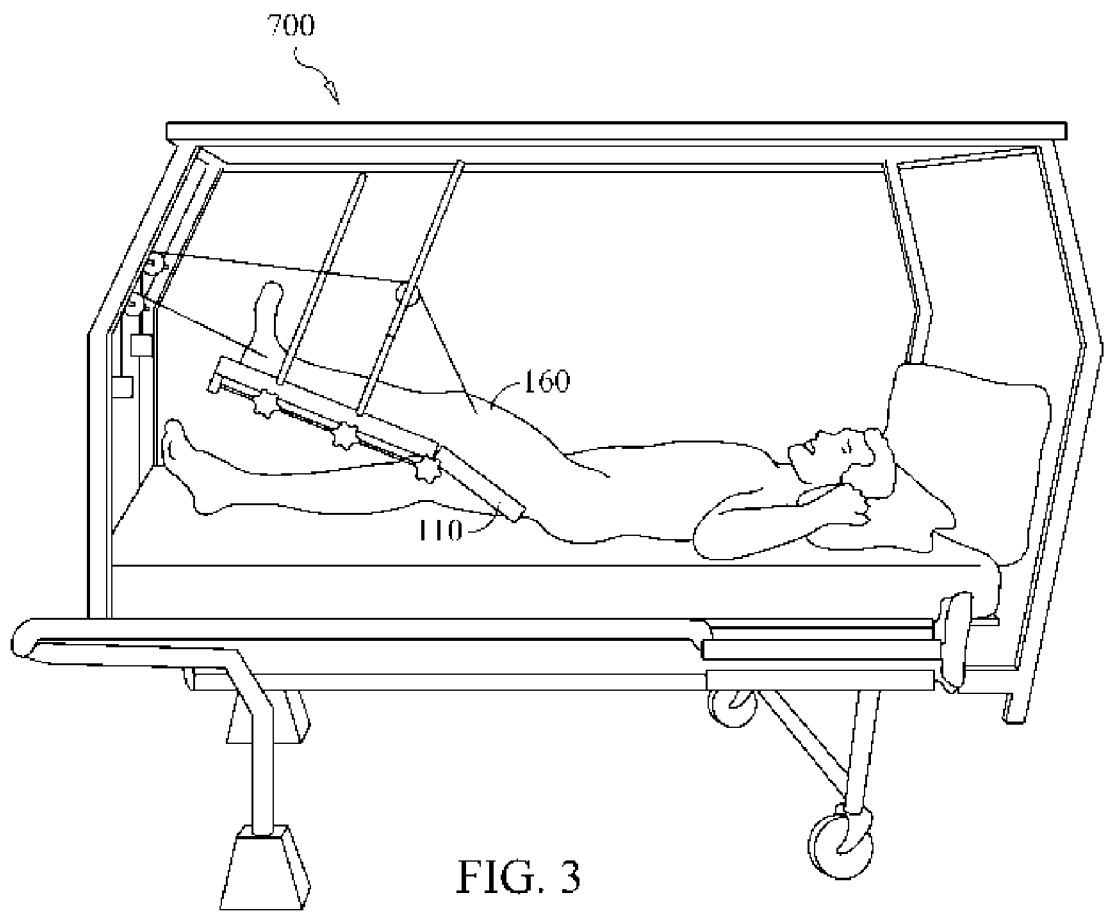
FIG. 3 shows a limb supporting splint of a portable splint system according to the present invention in an overhead traction apparatus.

The portable splint system 100 of the present invention has a limb supporting splint 110 having a proximal end 120 and a distal end 130. FIG. 1 shows a portable splint system 100 according to the present invention. The limb supporting splint 110 has a least two sections, each section has a substantially continuous cover plate 140, each cover plate 140 having a concave contoured upper surface 150 for cradling a splinted limb 160. A locking hinge 170 connects the sections of the limb supporting splint 110. The limb supporting splint 110 is suitable for use in a bed or overhead traction apparatus known in the art. FIG. 2 shows limb supporting splint 110 of a portable splint system 100 according to the present invention. FIG. 3 shows a limb supporting splint 110 according to the present invention in an overhead traction apparatus.

Figure 4:
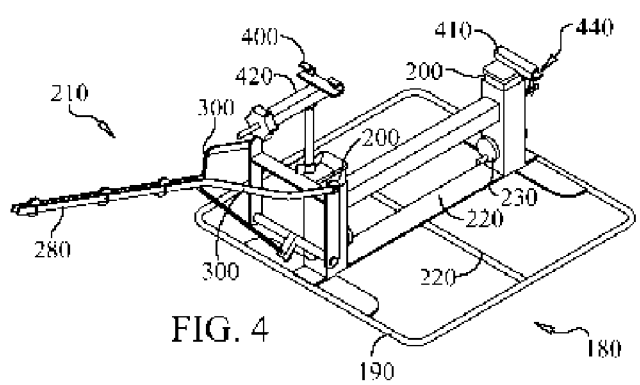
FIG. 4 shows a preferred embodiment of a portable base unit of a portable splint system according to the present invention.

The portable splint system 100 also includes a portable base unit 180 onto which the limb supporting splint 110 may be attached. FIG. 4 shows a preferred embodiment of a portable base unit 180 of a portable splint system 100 according to the present invention. Thus, the limb supporting splint 110 may be used in both an overhead traction system and as part of the portable splint system 100 of the present invention. The portable base unit 180 has a stabilizing frame 190, height adjusters 200 for independently adjusting the height of the proximal end 120 of the limb supporting splint 110 and the distal end 130 of the limb supporting splint 110, and traction weight supports 210.

In various preferred embodiments the stabilizing frame 190 is a substantially rectangular and has cross bracing 220 and provisions for mounting the height adjusters 200. Ideally, the stabilizing frame 190 is sized to fit onto a hospital bed or similarly sized object, such as a gurney, x-ray table, or the like. Furthermore, the stabilizing frame 190 should be sufficiently sized to resist movement and tipping of the portable splint system 100 while in use. Those skilled in the art will appreciate that the exact dimensions of the stabilizing frame 190 are not critical to present invention and can vary with the application and with the materials from which the present invention is constructed.

Figure 5:
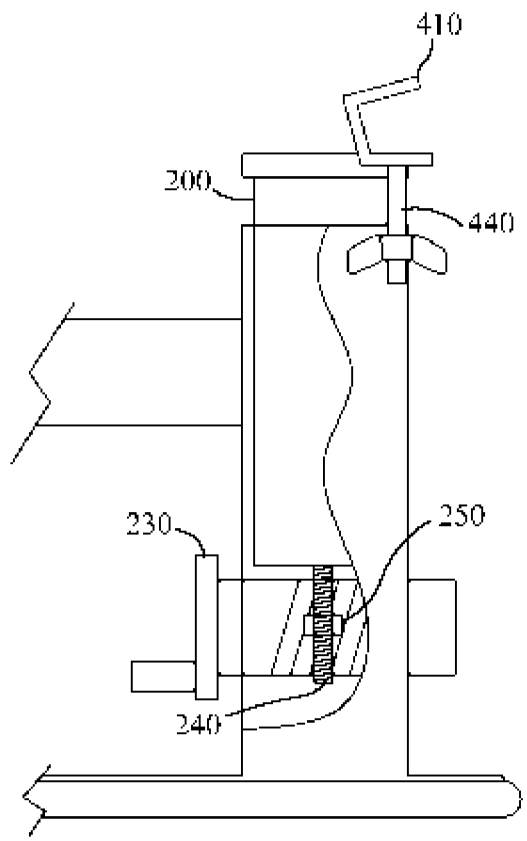
FIG. 5 shows a preferred embodiment of a height adjuster of a portable base unit of a portable splint system according to the present invention.

In various preferred embodiments the height adjusters 200 have a turnable portion, such as a crank 230, connected to a screw system 240 and a follower 250 connected to the screw system 240. Rotation of the crank 230 turns the screw system 240, which imparts a vertical displacement on the follower 250. FIG. 5 shows a preferred embodiment of a height adjuster 200 of a portable base unit 180 of a portable splint system 100 according to the present invention. Other types of height adjusters 200, known in the art, may also be used, including, but not limited to, slides locked in place by pins, turnbuckle arrangements, powered height adjusters, and the like. The height adjusters 200 allow for easy adjustment and elevation of the limb to help treat, among other things, preoperative and postoperative swelling.

Figure 6:
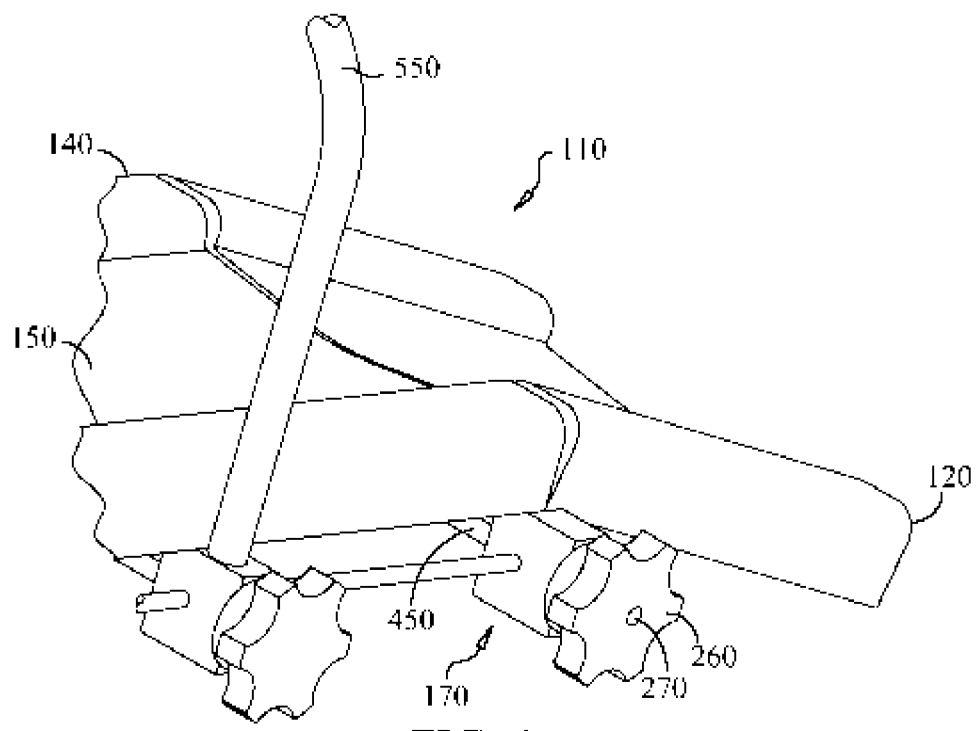
FIG. 6 shows a preferred embodiment of a locking hinge of a limb supporting splint of a portable splint system according to the present invention.

The locking hinge 170 connecting the sections of the limb supporting splint 110 can be of any type known in the art to keep the sections at a desired relative angle to one another. In various preferred embodiments, the locking hinge 170 has at least one turnable device, such as a knob 260, connected to a threaded member 270, where the knob 260 has open and closed or loose and locked positions. In the open or loose position, the sections are free to rotate to a desired relative angle between the sections and in the closed or locked position, the sections are unable to rotate. FIG. 6 shows a preferred embodiment of a locking hinge of a limb supporting splint of a portable splint system according to the present invention. The locking hinge 170 allows, among other things, for the treatment of patients with fused knees as well as helping comfortably maintain the fracture site during bed linen changes.

Figure 7:
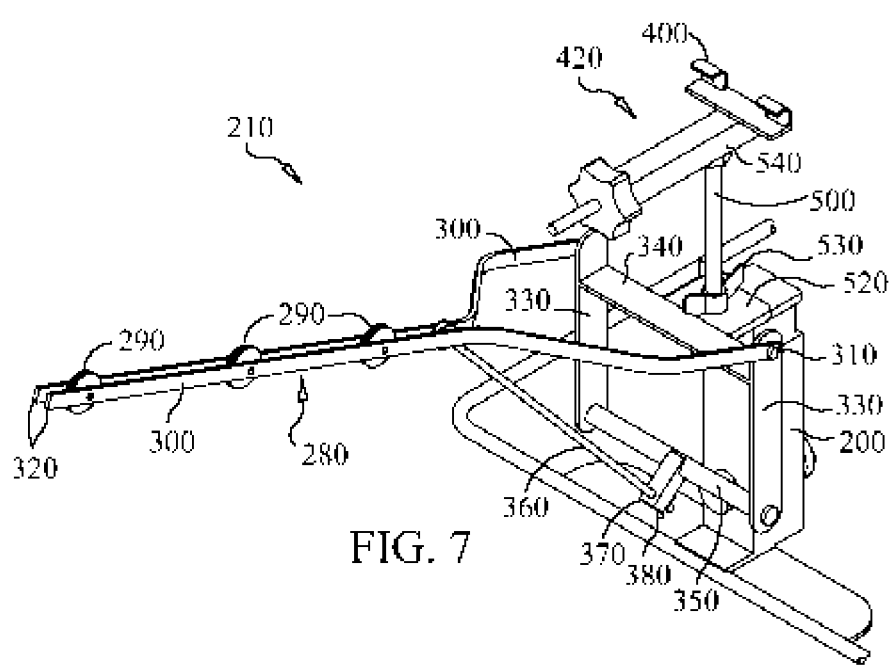
FIG. 7 shows a preferred embodiment of a traction weight bearing arm of a portable splint system according to the present invention.

The traction weight supports 210 preferably has a traction weight bearing arm 280, which has at least one pulley 290 disposed thereon. The pitch angle of the traction weight bearing arm 280 can be adjustable. Adjusting the pitch angle of the traction weight bearing arm 280 allows for more precise application of the direction of the traction force. In various preferred embodiments, the traction weight bearing arm is connected to the height adjuster 200 associated with the distal end 130 of the limb supporting splint 110. FIG. 7 shows a preferred embodiment of a traction weight bearing arm of a portable splint system according to the present invention. In other various preferred embodiments, the traction weight bearing arm 280 is constructed from two elongated bars 300, each having a first end 310 and a second end 320. Each of the first ends 310 can be connected to one of two vertical support bars 330, where vertical support bars 330 are separated by an upper horizontal support 340 and a lower horizontal support 350. The upper horizontal support 340 is attached to the attached to the height adjuster 200 associated with the distal end 130 of the limb supporting splint 110. The second ends 320 of the elongated bars 300 are free. The pulley or pulleys 290 can be disposed and secured between the elongated bars 300. The pitch angle of the traction weight bearing arm 280 can be adjusted using a threaded rod 360, where one end of the threaded rod 360 is attached to the elongated bars 300, and the other end of the threaded rod 360 is connected to a block 370 which freely rotates on said lower horizontal support 350, locking members, such as nuts 380, on the threaded rod 360 secure the threaded rod 360 relative to the block 370. Multiple pulleys 290 allow for the treatment of multiple fracture sites. For example, a patient with a pelvic fracture and a tibia fracture can by treated using the same system 100. Other systems to support and adjust traction weights, known in the art, may also be used.

The limb supporting splint 110 can be attached to the portable base unit 180 in a variety of ways. In various preferred embodiments, a distal facing hook 400 associated with the height adjuster 200 associated with the distal end 130 of the limb supporting splint 110 and a proximal facing hook 410 associated with the height adjuster 200 associated with the proximal end 120 of the limb support splint 110 are used to connect the portable base unit 180 to the limb supporting splint 110. In this arrangement, a distal clamping system 420 is used to secure a distal connecting rod 430 on the limb supporting splint 110 into the distal facing hook 410 and a proximal clamping system 440 is used to secure a proximal connecting rod 450 on the limb supporting splint 110.

The proximal clamping system 440 and the distal clamping system 420 can be any type of clamp known in the art. In various preferred embodiments, the distal clamping system 420 has a threaded rod 500 inserted into an opening (not shown) on a top side 520 of the height adjuster 200 associated with the distal end 130 of the limb supporting splint 110, where the threaded rod 500 has a nut 530 or other locking mechanism to control the height of the threaded rod 500. A horizontally adjustable member 540 is mounted on top of the threaded rod 500 such that distal movement of the horizontally adjustable member 540 pulls the distal facing hook 400 onto the distal connecting rod 430, which in turn pulls the proximal connecting rod 450 into the proximal facing hook 410.

The limb supporting splint 110 may also have one or more vertical support arches 550 mounted thereon. The vertical support arches 550 may be fixed to the limb supporting splint 110 or removable. The vertical support arches 550 may have one or more pulleys 290 mounted thereon to assist in the application of traction force to the patient. Furthermore, the vertical support arches 550 may be adjustable in height. Height variation can be accomplished through any means known in the art, such as the arch having slidably adjustable portions secured in place using pins (not shown) or spring loaded balls (not shown). Other height adjustment systems known in the art may also be used.

Figure 8:
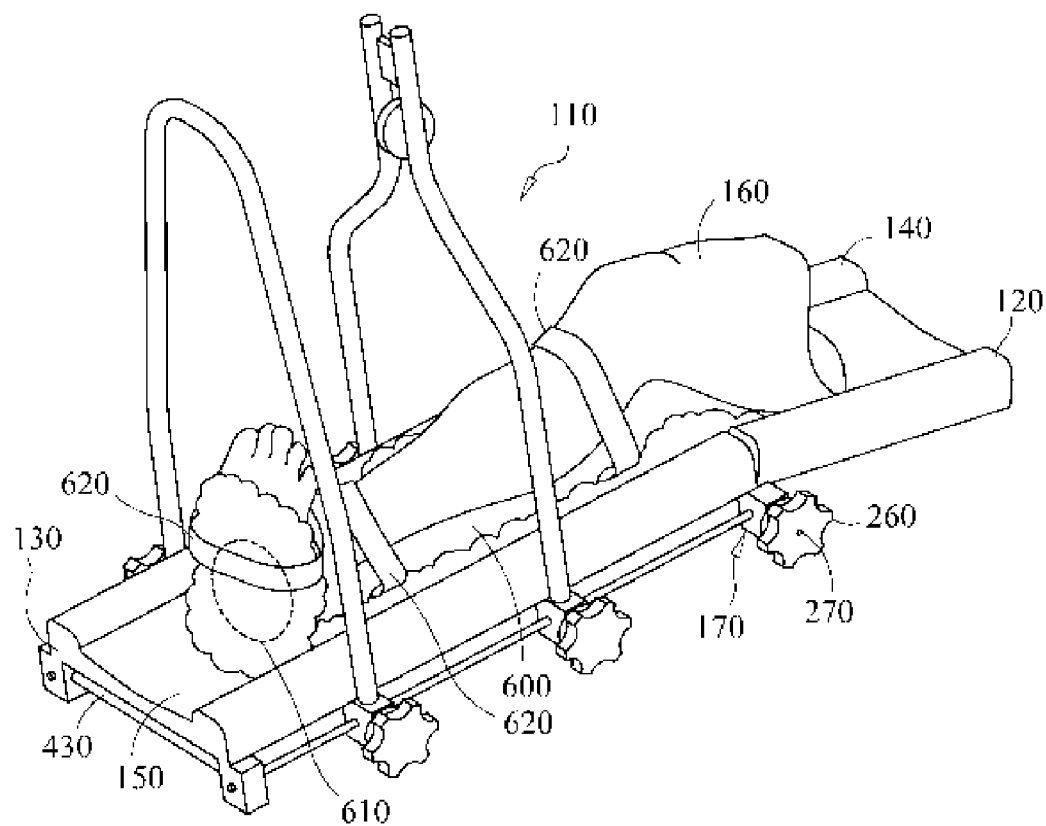
FIG. 8 shows a preferred embodiment of pad for a limb supporting splint of a portable splint system according to the present invention.

A pad 600 may be placed between the limb supporting splint 110 and the splinted limb 160. FIG. 8 shows a preferred embodiment of pad for a limb supporting splint of a portable splint system according to the present invention. For example, when the splinted limb 160 is a leg, the pad 600 may extend from thigh region at or about the proximal end 120 of the limb supporting splint 110 to the foot region at or about the distal end 130 of the limb supporting splint 110. This pad 600 can be constructed from materials known in the art, including, but not limited to, a cloth or sheepskin covering over foam padding. Pad 600 can further help to improve circulation in the splinted limb 160 and reduce the occurrence of DVT by reducing pressure points.

The pad 600 can be equipped with one or more bladders 610 capable of being periodically or intermittently inflated and deflated with air or another working fluid known in the art. An electrically powered air pump (not shown) or other similar devices known in the art can be used to inflate and deflate the one or more bladders 610. Periodic or intermittent inflation and deflation of the one or more bladders 610 can further help to improve circulation in the splinted limb 160 and reduce the occurrence of DVT. The pad 600 can be secured to the splinted limb 160 with straps 620 that wrap around the splinted limb 160 such that the bladders 610, when inflated, impart a compressive force to the splinted limb 160.

In various preferred embodiments, the pad 600 has at least one bladder 610 located in the region of the instep of the foot when the splinted limb 160 is a leg.

In addition to the system 100 described above, the present invention also includes a method of transferring a splinted patient from a bed mounted traction apparatus 700 to a portable splint system 100. First, a limb supporting splint 110 in a bed mounted traction apparatus 700 is secured to a portable base unit 180. Next, traction force from the bed mounted traction apparatus 700 is transferred to the portable base unit 180 without removal of the traction force. By using this method, continuous traction is maintained, which reduces the chances of a fracture collapse, bleeding and deep vein thrombosis.

While specific embodiments have been illustrated and described, numerous modifications come to mind without significantly departing from the spirit of the invention and the scope of protection is limited by the scope of the accompanying claims.

What is claimed is:

1. A portable splint system comprising:
    a limb supporting splint comprising a proximal end and a distal end, said splint comprising a least two sections, each section having a substantially continuous cover plate, each cover plate having a concave contoured upper surface for cradling a splinted limb, and a locking hinge connecting said sections,
    a substantially rigid single piece portable base unit having means for detachably connecting said portable base unit to said limb supporting splint, means for independently adjusting the height of said proximal end and means for independently adjusting the height of said distal end, a stabilizing frame, and means for supporting at least one traction weight, said limb supporting splint being adapted to support a leg portion and foot of a patient, and adapted to detach from said base and be used in conjunction with separate traction means,
    wherein said system is configured to be self-supporting without requiring an overhead frame,
wherein said means for supporting at least one traction weight comprises:
    a traction weight bearing arm having at least one pulley disposed thereon, means for adjusting a pitch angle of said traction weight bearing arm, and
    said weight bearing arm connected to said means for independently adjusting the height of said distal end,
    wherein said traction weight bearing arm comprises:
    two elongated bars, each having a first and second ends, each of said first ends being attached to one of two vertical support bars, said vertical support bars being separated by upper and lower horizontal supports, said upper horizontal support being attached to said means for independently adjusting the height of said distal end, said second ends being free, said at least one pulley is disposed and secured between said elongated bars, and said means for adjusting a pitch angle of said traction weight bearing arm comprising a threaded rod, wherein a first end of said threaded rod is attached to said elongated bars, and a second end of said threaded rod is connected to a block which freely rotates on said lower horizontal support, locking means on said threaded rod secure said threaded rod relative to said block.

2. A portable splint system comprising:
    a limb supporting splint comprising a proximal end and a distal end, said splint comprising a least two sections, each section having a substantially continuous cover plate, each cover plate having a concave contoured upper surface for cradling a splinted limb, and a locking hinge connecting said sections,
    a substantially rigid single piece portable base unit having means for detachably connecting said portable base unit to said limb supporting splint, means for independently adjusting the height of said proximal end and means for independently adjusting the height of said distal end, a stabilizing frame, and means for supporting at least one traction weight, said limb supporting splint being adapted to support a leg portion and foot of a patient, and adapted to detach from said base and be used in conjunction with separate traction means,
    wherein said system is configured to be self-supporting without requiring an overhead frame,
wherein said means for cooperatively connecting said portable base unit to said limb supporting splint comprises:
    a distal facing hook connected to said means for independently adjusting the height of said distal end, and a proximal facing hook connected to said means for independently adjusting the height of said proximal end,
    clamping means for securing a distal connecting rod on said limb supporting splint into said distal facing hook, and
    clamping means for securing a proximal connecting rod on said limb supporting splint into said proximal facing hook.

3. The portable splint system according to claim 2, wherein said clamping means for securing said distal connecting rod on said limb supporting splint into said distal facing hook comprises:
    a threaded rod inserted into an opening on a top side of said means for independently adjusting the height of said distal end,
    locking means on said threaded rod to adjustably control the height of said treaded rod, and
    a horizontally adjustable member atop said threaded rod, wherein distal movement of said horizontally adjustable member pulls said distal facing hook onto said distal connecting rod which in turn pulls said proximal connecting rod into said proximal facing hook.

4. A method of transferring a splinted patient from a bed mounted splint to a portable splint system comprising:
    securing a limb supporting splint, wherein said limb supporting splint is supporting a limb of said splinted patient in a bed mounted traction apparatus, to a self supporting portable base unit,
    transferring traction force from said bed mounted traction apparatus to said portable base unit without removing the traction force applied to the limb.

* * * * *